(12) United States Patent
Perrier et al.

(10) Patent No.: US 9,022,964 B2
(45) Date of Patent: May 5, 2015

(54) METHOD AND APPARATUS FOR ORTHOPEDIC CAST REMOVAL UTILIZING A ROTARY IMPACT DRIVER

(71) Applicants: Gregory Perrier, Dix Hills, NY (US); John Mizzi, Poughkeepsie, NY (US)

(72) Inventors: Gregory Perrier, Dix Hills, NY (US); John Mizzi, Poughkeepsie, NY (US)

( * ) Notice: Subject to any disclaimer, the term of this patent is extended or adjusted under 35 U.S.C. 154(b) by 105 days.

(21) Appl. No.: 13/870,532

(22) Filed: Apr. 25, 2013

(65) Prior Publication Data

US 2013/0296753 A1  Nov. 7, 2013

Related U.S. Application Data

(60) Provisional application No. 61/639,679, filed on Apr. 27, 2012.

(51) Int. Cl.
*A61F 5/00* (2006.01)
*A61F 15/02* (2006.01)

(52) U.S. Cl.
CPC ..................................... *A61F 15/02* (2013.01)

(58) Field of Classification Search
CPC . A61F 15/02; A61F 13/04; A61F 2002/1686; A61F 5/04; B21F 1/02; B23K 9/1333; B23K 9/1336; B23K 9/125; B23K 20/12; B23K 20/1245; B23K 20/126; B23K 37/0211; B23K 37/0282; B21C 47/14

USPC ............................................. 602/8–9, 5
See application file for complete search history.

(56) References Cited

U.S. PATENT DOCUMENTS

| | | | | |
|---|---|---|---|---|
| 1,967,888 A | * | 7/1934 | Kearsley | 30/1 |
| 2,070,358 A | * | 2/1937 | Hengstenberg | 30/370 |
| 3,085,569 A | * | 4/1963 | Cook et al. | 602/9 |
| 3,307,537 A | * | 3/1967 | Simon et al. | 602/8 |
| 3,867,931 A | * | 2/1975 | Babka | 602/9 |
| 4,227,517 A | | 10/1980 | Aguiar | |

FOREIGN PATENT DOCUMENTS

GB            731182         * 11/1953

* cited by examiner

*Primary Examiner* — Michael Brown
(74) *Attorney, Agent, or Firm* — Alfred M Walker

(57) ABSTRACT

An orthopedic cast removal tool and method uses an unmodified, typically cordless, rotary impact driver and a embedded wire to cut through an orthopedic cast for removal. By merging it with a slotted spacer block specifically for this cast removal purpose, an ergonomic tool is provided which allays fears of orthopedic patients. When rotating and encountering high resistance of the plaster or fiberglass material of the cast, the cordless rotary impact driver does not bog down; since it seamlessly engages impact action, which offers an order of magnitude or more torque multiplication via short frequent pulses (several per second) to overcome this torque resistance. Thus a high amount of torque with very little reaction force is made available to cut through a cast while affording the technician good control. The cast is cut very rapidly with little dust creation and no jostling of the patient.

5 Claims, 4 Drawing Sheets

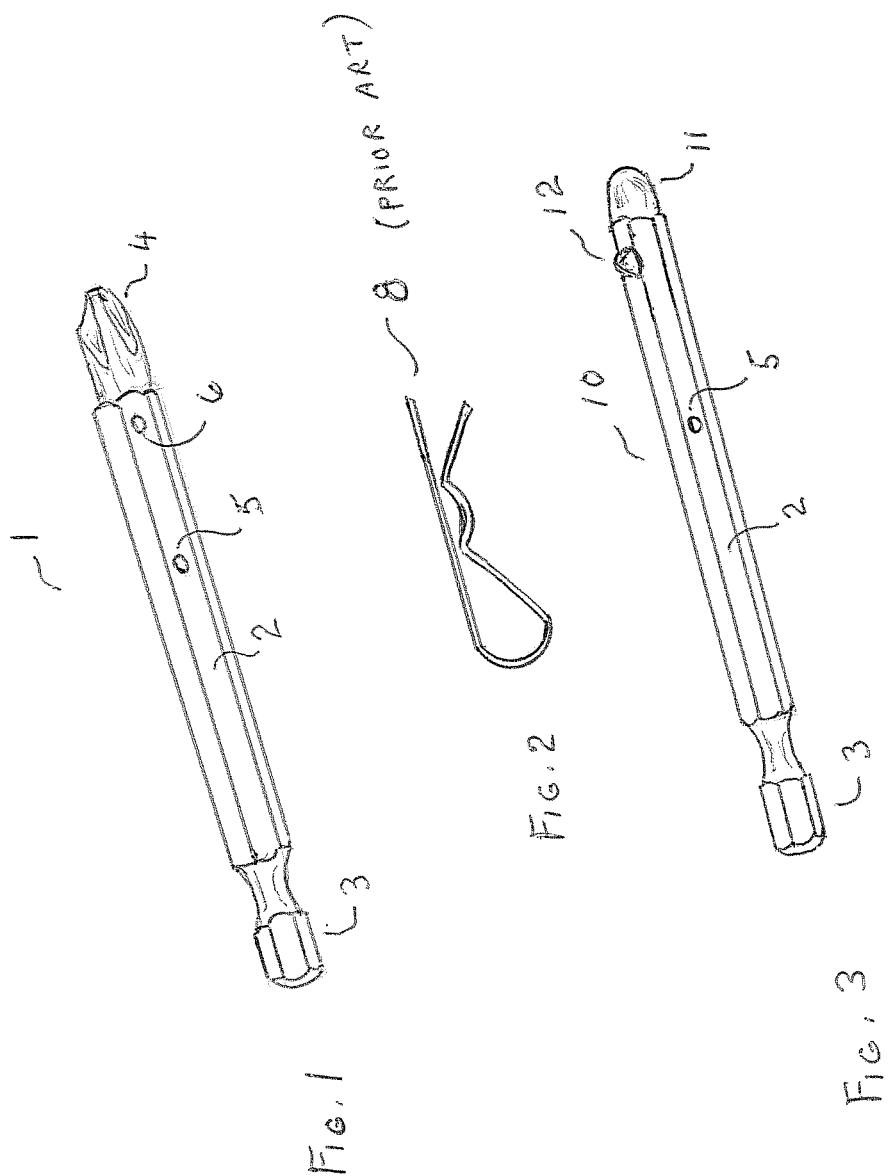

FIG. 8   PROCEDURE STEP CHART

*CAST SETTING STEPS:*

*1. Remove liner from tape of wire package.*

*2. Attach wire to patient appendage using tape, making sure to bridge fracture region.*

*3. Use normal procedure to apply cast material to patient appendage over previously attached removal wire. While applying cast, embed anchor end of wire in cast and bend free end of wire up to expose approximately 3" beyond top of finished cast surface. Tuck free end of wire into surface of cast before solidifying.*

*CAST CUTTING STEPS (for removal):*

*1. Pry end of wire free of cast surface.*

*2. Place tip of wire through wire hole of mandrel and wind once manually.*

*3. Engage mandrel with chuck of rotary impact driver.*

*4. Feed mandrel distal end through spacer block bearing and lock in place by guiding wire through wire slot in spacer block and then using retainer clip in mandrel hole visible near outer bearing surface. At this point, wire is still attached to patient and mandrel, spacer block, and rotary impact driver are all attached together.*

*5. Activate driver to wind wire onto mandrel thereby moving spacer block along cast while wire cuts through cast.*

*6. Remove retainer clip from mandrel after cut and pull driver away from spacer block.*

*7. Separate spacer block and set aside, then disengage mandrel from driver chuck.*

*8. Pry cast apart at cut.*

METHOD AND APPARATUS FOR ORTHOPEDIC CAST REMOVAL UTILIZING A ROTARY IMPACT DRIVER

RELATED APPLICATIONS

This application is based upon provisional patent application Ser. No. 61/639,679 filed on Apr. 27, 2012, and claims priority therefrom, pursuant to 28 U.S. Code §119(e). That application is incorporated by reference herein.

BACKGROUND OF THE INVENTION

Electrically driven saws are generally used for removing plaster or resin type orthopedic casts on human limbs or appendages. A cut is made and then the cast is split for removal. The process itself is not pleasant for the patient. Pediatric patients are often intimidated by the sawing. The saws are noisy and usually produce much dust in the cutting operation.

The prior art shows an alternate method that involves the use of an embedded wire or strand which is attached to the surface of a patients limb prior to embedding in the cast itself. By pulling the wire through the cast, the cutting action will separate the cast for removal thereby avoiding the use of a saw with its noise and dust drawbacks.

Babka in his U.S. Pat. No. 3,867,931 describes a method for removing an orthopedic cast utilizing an embedded wire which is pulled through the thickness of the cast by manually operated ratchet apparatus. This tends to be a slow operation which also transfers substantial reaction force and torque to the patient during the removal process.

An improved wire cast cutting system is revealed in U.S. Pat. No. 4,227,517 of Aguiar. It involves the use of a battery operated device using a gear motor to pull the embedded wire at an acute angle through a low friction guide plate resting on the surface of the cast. This greatly reduces the jostling of the patient by the procedure since the pulling force is localized to the tool. The tool is grasped by the technician and moves along the cast as the cutting action progresses. A combination of large numerical gear reduction ratio and substantial motor power is required to perform the cutting operation at a timely rate. Both of these requirements indicate that the specially designed removal device drive head as well as its battery supply may be bulky and expensive. The wire pulling force must overcome any resistance as provided by the hardest and most difficult region of the cast encountered along the pulling path. The torque provided by the removal tool must match and overcome this worst-case resistance to prevent bogging down and stopping.

OBJECTS OF THE INVENTION

It is therefore an object of the present invention to provide a safe and efficient method for orthopedic cast removal.

It is also an object of the present invention to provide an orthopedic cast removal tool which allays the fears of orthopedic patents subject to noisy and spinning buzz saw type of cast removal devices.

It is yet another object of the present invention to provide an ergonomic orthopedic cast removal tool with attractive performance attributes results.

It is a further object of the present invention to provide an orthopedic cast removal tool which does not bog down while encountering high resistance and which seamlessly engages impact action which offers an order of magnitude or more torque multiplication via short frequent pulses to overcome this torque resistance.

It is also an object of the present invention to provide an orthopedic cast removal tool which is able to cut through a cast very rapidly with little dust creation and no jostling of the patient.

Other objects which become apparent from the following description of the present invention.

SUMMARY OF THE INVENTION

While similar to earlier attempts utilizing an embedded wire to cut through an orthopedic cast for removal, the use of an unmodified rotary impact driver as the basis for the apparatus offers several advantages. This type of tool is currently manufactured by several companies in a battery operated cordless variety for general construction and household use. It is therefore quite inexpensive as compared to a specialized medical tool. An example of this type of tool is a HITACHI® model WH 10DFL Cordless Impact Driver. By merging it with a simple slotted spacer block and mandrel developed for this cast removal application, an ergonomic tool with attractive performance attributes results.

The cordless rotary impact driver when rotating a bit and encountering high resistance does not simply bog down and stop; it seamlessly and automatically engages rotary impact action which offers an order of magnitude or more torque multiplication via short frequent pulses (several per second) to overcome this torque resistance. Thus a high amount of torque with very little reaction torque through the handle is made available to cut through a cast at a particularly difficult region. The low reaction torque affords the technician good control whether zipping through the low-torque regions or automatically slowing down the action to pulse through a tough region. The cast is cut very rapidly with little dust creation, noise, and no jostling of the patient.

The apparatus includes an unmodified cordless rotary impact driver, a wire winding mandrel, and a slotted spacer block. The mandrel can be a standard Phillips screw driver bit with two transverse holes added, one to accommodate the wire end and another to accept a spring clip for locking the slotted spacer block. Alternatively, a custom-made self-locking mandrel with a spring-loaded ball near the distal end can be used, dispensing with the spring clip. The slotted spacer block supports the winding mandrel in a bearing at the distal end and has a base which slides along the surface of the cast while in use; it also has an area to accept the wire as it is wound onto the mandrel. The slot is to permit the wire end to be slipped into the winding cavity after the end has been manually started onto the mandrel.

The wire is supplied mounted onto a release substrate which is peeled off a tape prior to using the same wire-attached tape to attach the wire to the patient prior to embedding it in the cast material. If the release substrate is semi-rigid, the mounted wire (which is not springy) will have less tendency to be bent before use. A free end of the wire is bent away from the patient and will rise beyond the finished cast by about 3". It is then bent over and embedded near the outer surface of the cast so that it can be easily exposed prior to removal. The distal end of the wire is looped into a cast-engaging configuration free of tape so that it acts as an anchor to resist pulling through during the removal phase.

BRIEF DESCRIPTION OF THE DRAWINGS

The present invention can best be understood in connection with the accompanying drawings. It is noted that the invention is not limited to the precise embodiments shown in drawings, in which:

FIG. 1 is a perspective view of a winding mandrel made from a modified Phillips screwdriver bit with a hex shank;

FIG. 2 is a side elevation of a spring clip of the type that can be used with the mandrel of FIG. 1 to lock the spacer block in place;

FIG. 3 is a perspective view of a custom-made mandrel with self-locking spring loaded ball near distal end;

FIG. 8 is a procedure step chart guiding the casting process as well as the cast cutting process using the method and apparatus of this invention.

DETAILED DESCRIPTION OF THE INVENTION

Figure 5:
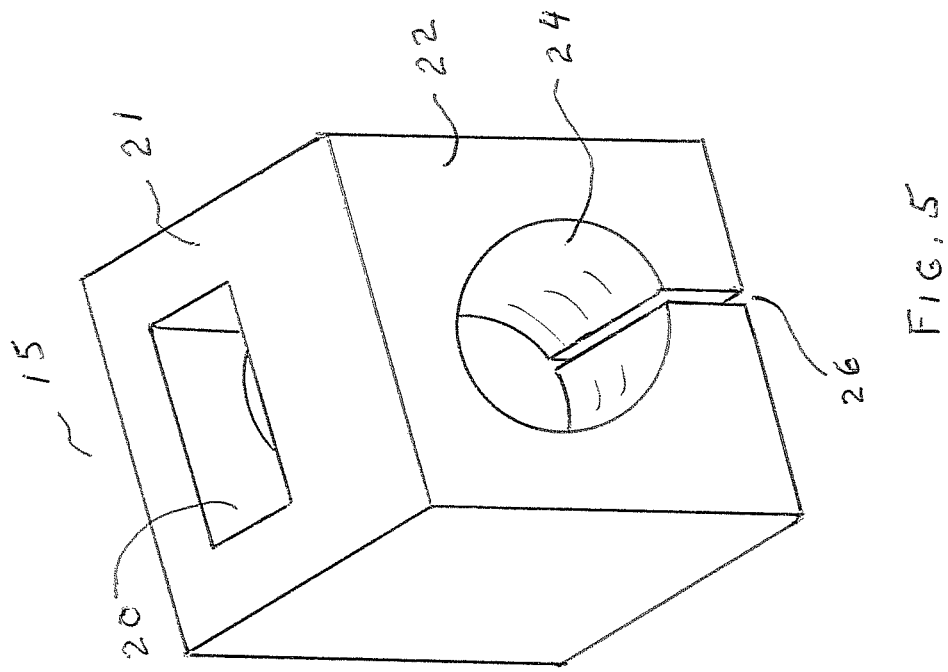
FIG. 5 is a perspective view of the slotted spacer block showing the rotary impact driver access hole and wire slot at the rear.

The apparatus of this invention comprises several parts. The wire winding mandrel 1 is shown at FIG. 1. In this case mandrel 1 is simply an ordinary Phillips screw driver bit compatible with a rotary impact driver with chucking end 3 hexagonal crossectional shaft 2 and driver end 4 with the addition of two transverse holes. Hole 5 is to engage the free end of the cutting wire and hole 6 is to accommodate locking clip 8 as shown in FIG. 2. An alternate embodiment of mandrel 10 is shown in FIG. 3. This also has the chuck engagement features 3, the hexagonal shaft 2 and wire end hole 5, but instead of a second hole an automatic self-locking spring-loaded ball 12 is used near the distal end which is now just a rounded contour 11. When using mandrel 10, no locking clip is used. It is simply snapped through the bearing hole in the slotted spacer block bearing.

Figure 4:
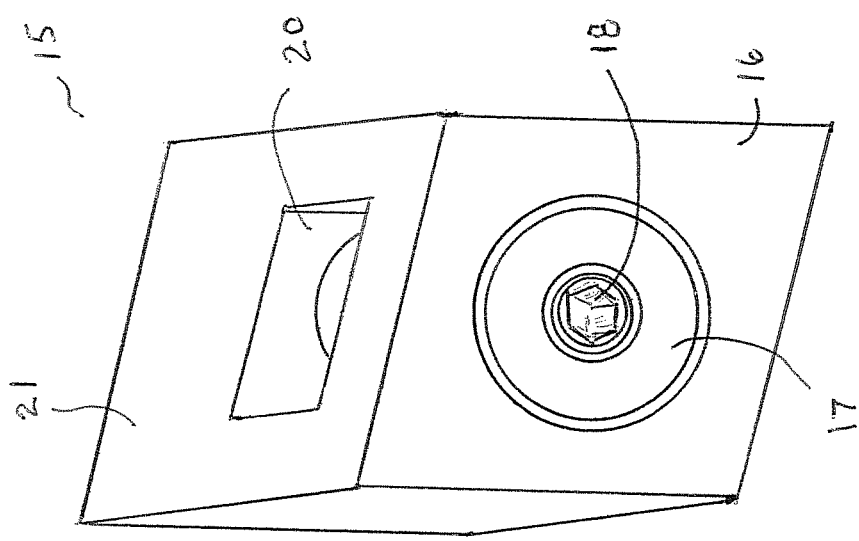
FIG. 4 is a perspective view of a slotted spacer block showing the front face with ball bearing for support of the mandrel.

Slotted spacer block 15 is shown in FIGS. 4 and 5. The front face 16 of FIG. 4 is shown to have a mounted ball bearing 17 with a six-sided central hole 18 to accommodate the hexagonal shaft 2 of the winding mandrel. This bearing supports the distal end of wire winding mandrel 1 or 10. Top surface 21 shows rectangular hole 20 which acts as a cavity to contain the cutting wire as it is wound onto mandrels 1 or 10. FIG. 5 shows the rear face 22 which has the rotary impact tool access hole 24 with wire access slot 26. Note that the bottom surface of spacer block 15 rides along the outer cast surface during the cutting phase. Block 15 is preferably injection molded or machined from a strong impact resistant plastic resin such as glass reinforced Nylon, ABS, or polyester.

Figure 6:
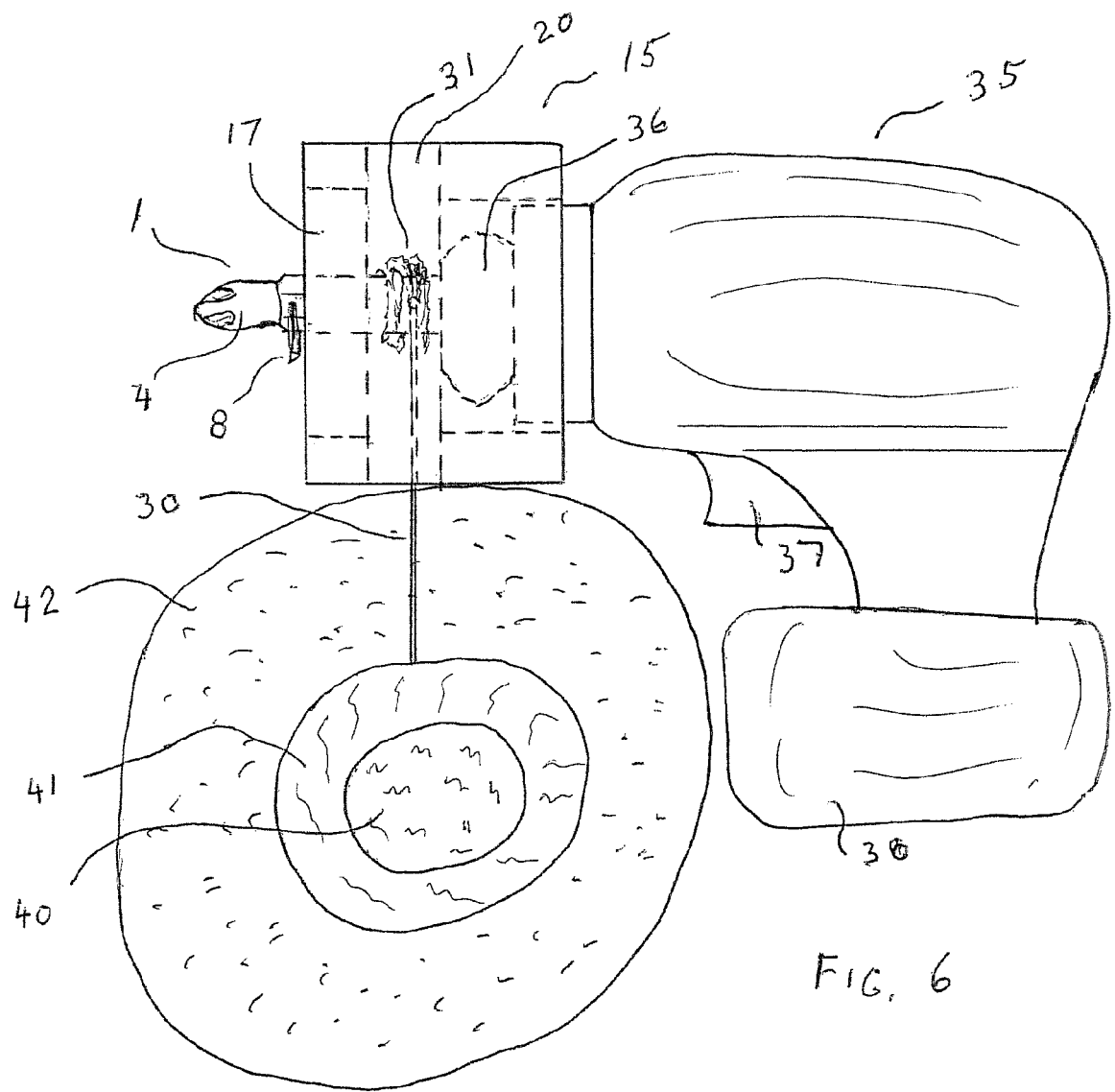
FIG. 6 is an end view showing the placement of the apparatus atop a limb cast during a cast cutting operation, wherein the limb and cast are shown in crossection.

FIG. 6 shows a limb (bone 40 and flesh/tissue 41) with a cast 42 on it in crossection. Atop cast 42 is shown an assembly of rotary impact driver 35 with trigger 37, battery pack 38, and hex bit chuck 36. Unlike a traditional round crossection drill bit chuck, hex bit chuck 36 is actually a metal hex coupler providing quick insertion and removal of compatible hex crossection bits such as wire mandrels 1 or 10. Note that mandrel 1 is engaged in chuck 36 and passes through bearing 17 of slotted spacer block 15. Note that locking spring clip 8 locks together mandrel 1, rotary impact driver 35 and slotted spacer block 15 as a unit. Wire 30 is shown being wound 31 onto mandrel 1 within rectangular hole 20 of block 15; this is the cutting phase.

Figure 7:
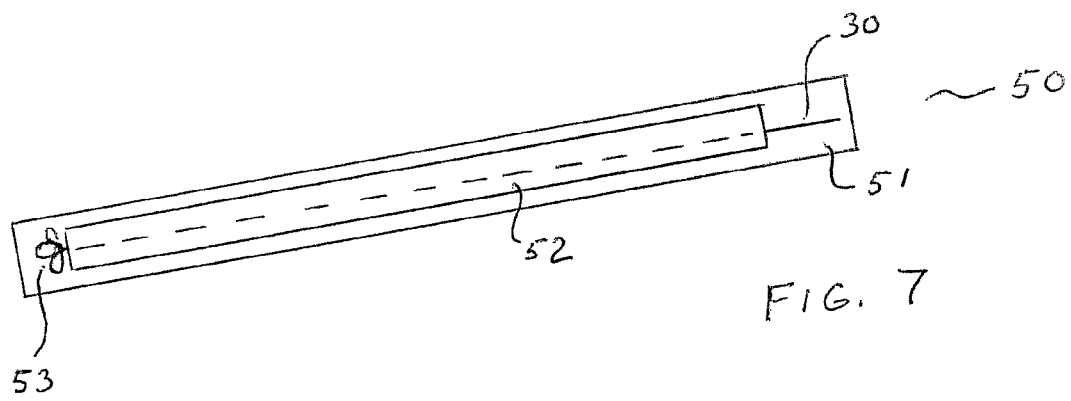
FIG. 7 is a top elevation of a packaged wire as used in this invention.

FIG. 7 shows the packaged cutting wire 30 as taped via tape 52 onto semi-rigid release liner 51. Note free end beyond tape 52 and looped anchor distal end 53.

FIG. 8 details the steps in the method of this invention. Three steps are involved in handling the cutting wire in the cast setting phase. While removing the liner from the wire package in step 1, the tape should not be removed from the wire since it will be used to attach to the patient's limb in step 2.

The 8 steps detailing the cutting of the cast by the cutting wire are also listed in FIG. 8. It may be found through experience that other ways of accomplishing the task may be more effective, but these steps in this order accomplish the objective. The cutting wire may dislodge automatically from the cast at the end of the cut, this would be preferable. In that case, it is simply pulled through, the back of the slotted spacer block after the block is disengaged from the mandrel. If the wire is still attached to some cast remnant, reversing the impact tool momentarily and using a cutting pliers may be required to disengage the impact driver with attached mandrel.

After the impact tool with mandrel bit in chuck is free of the slotted spacer block, the mandrel can be simply de-chucked as any other tool bit with the spent wire still wound on it. A new mandrel bit can then be used for the next cast removal procedure. In this manner, the rotary impact tool can be quickly re-used as in a "production line" environment as long as several mandrels are available. The wire may be unwound from a used mandrel manually or by chucking in a simple cordless screwdriver and driving in reverse while holding the wire end in a pair of pliers. The cordless impact tool itself may be used in reverse to unwind used wire, but a slow cordless screwdriver may be safer in this operation.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

The invention claimed is:

1. Cast removal apparatus for an orthopedic cast enclosing a limb, said cast removal apparatus comprising:
    a) an unmodified rotary impact driver;
    b) a cast-embedded wire adapted to be embedded within an orthopedic cast enclosing a limb;
    c) a wire winding mandrel bit; and,
    d) a slotted spacer block, wherein said mandrel bit is engaged in a chuck of said unmodified rotary impact driver and upon rotational activation of said unmodified rotary impact driver said cast-embedded wire engaged through a hole of said mandrel bit, said wire being wound onto said mandrel bit within a central cavity of said slotted spacer block as said wire is pulled by said rotating mandrel bit, thereby cutting said cast in a severance line in a cutting phase.

2. The cast removal apparatus as in claim 1 further comprising said spacer block spacing said wire winding mandrel away from an outer surface of said cast and supporting a distal end of said wire winding mandrel in a rotary bearing.

3. The cast removal apparatus as in claim 2 wherein said rotary bearing is a ball bearing.

4. The cast removal apparatus as in claim 1 wherein said wire is packaged as an attachment unit with a tape, a release liner, and a formed distal anchor.

5. A method for installing and removing an orthopedic cast comprising the steps of:
- a) attaching a wire to a patient's limb or appendage, bridging a fracture region thereof;
- b) applying orthopedic cast material over said patient's limb or appendage and over said wire, and while applying said cast, embedding an anchor end of said wire in said cast and bending a free end of said wire up to expose said free end of said wire beyond a top of a finished surface of said cast, and tucking said free end of said wire onto said surface of said cast before said cast solidifies;
- c) when said cast is ready for removal, prying said free end of said wire away from said outer surface of said cast;
- d) placing a tip of said free end of said wire through a wire hole of a mandrel and winding said wire once manually;
- e) engaging said mandrel bit into said chuck of a rotary impact driver;
- f) guiding said wire through a slot in said spacer block then feeding a distal end of said mandrel through a bearing of said spacer block and locking said mandrel in place by using a retainer clip in a mandrel hole visible near an outer surface of said bearing, wherein said wire is still attached to said patient's limb or appendage and said mandrel, said spacer block and said rotary impact driver are all attached together;
- g) activating said rotary impact driver to wind said wire onto said mandrel, thereby moving said spacer block along an axis of said orthopedic cast while said wire cuts through said orthopedic cast;
- h) removing said retainer clip from said mandrel after cutting said orthopedic cast and pulling said rotary impact driver away from said spacer block;
- i) separating said spacer block and setting said spacer block aside, then disengaging said mandrel from said chuck of said rotary impact driver; and,
- j) prying said cut cast apart at said axial cut of said orthopedic cast and removing said orthopedic cast from the limb or appendage of the patient.

* * * * *